(12) United States Patent
Suarez et al.

(10) Patent No.: US 9,421,119 B2
(45) Date of Patent: *Aug. 23, 2016

(54) CERVICAL COLLAR BRACE WITH CABLE ADJUSTMENT

(71) Applicant: OPTEC USA, INC., Lawrenceville, GA (US)

(72) Inventors: Daniel Suarez, Lawrenceville, GA (US); Brent Rosendahl, Lawrenceville, GA (US)

(73) Assignee: OPTEC USA, INC., Lawrenceville, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/293,535

(22) Filed: Jun. 2, 2014

(65) Prior Publication Data

US 2014/0323938 A1      Oct. 30, 2014

Related U.S. Application Data

(63) Continuation of application No. 13/683,528, filed on Nov. 21, 2012, now Pat. No. 8,740,830, which is a continuation-in-part of application No. 13/451,704, filed on Apr. 20, 2012, now Pat. No. 8,864,693.

(51) Int. Cl.
*A61F 5/055*      (2006.01)

(52) U.S. Cl.
CPC ....................... *A61F 5/055* (2013.01)

(58) Field of Classification Search
CPC combination set(s) only.
See application file for complete search history.

(56) References Cited

U.S. PATENT DOCUMENTS

| 7,676,234 B2 * | 3/2010 | Harris ............................. 455/466 |
| 8,740,830 B2 * | 6/2014 | Suarez ..................... A61F 5/055 128/DIG. 23 |
| 8,864,693 B2 * | 10/2014 | Suarez ..................... A61F 5/055 128/DIG. 23 |
| 2007/0027418 A1 | 2/2007 | Calco et al. |
| 2013/0060179 A1 * | 3/2013 | Modglin ......................... 602/18 |

FOREIGN PATENT DOCUMENTS

| WO | WO 2008/033963 A2 | 3/2008 |
| WO | WO 2013/036368 A1 | 3/2013 |

OTHER PUBLICATIONS

European Patent Office; Extended European Search Report for Application No. 13164478.3; Jul. 31, 2013.

* cited by examiner

*Primary Examiner* — Ophelia A Hawthorne
(74) *Attorney, Agent, or Firm* — Gardner Groff Greenwald & Villanueva, P.C.

(57) ABSTRACT

A cervical collar brace including a main body collar, a first chin side support pivotally mounted to the main body collar, and a second chin side support pivotally mounted to the main body collar. A cable adjuster adjustably secures the first and second chin side supports to the main body collar and includes a rotatable wheel, one or more cables, and one or more lift effectors for lifting the chin side supports in response to rotation of the rotatable wheel in a first rotation direction. A chin piece is provided for supporting a wearer's chin.

16 Claims, 12 Drawing Sheets

CERVICAL COLLAR BRACE WITH CABLE ADJUSTMENT

CROSS-REFERENCE TO RELATED APPLICATION

This application claims the priority benefit of U.S. Non-Provisional patent application Ser. No. 13/683,528, now U.S. Pat. No. 8,740,830 filed Nov. 21, 2012, and which application is hereby incorporated herein by reference, and which application is a continuation-in-part application of U.S. Non-Provisional patent application Ser. No. 13/451,704, now U.S. Pat. No. 8,864,693 filed on Apr. 20, 2012, and which is also hereby incorporated herein by reference.

TECHNICAL FIELD

The present invention related to an orthopedic brace and in particular relates to cervical collar.

SUMMARY OF THE INVENTION

Briefly described, in a preferred form, the present invention comprises a cervical collar brace including a main body collar, a first chin side support pivotally mounted relative to the main body collar, and a second chin side support pivotally mounted relative to the main body collar. A cable adjuster is provided for adjustably securing the first and second chin side supports to the main body collar, with the cable adjuster including a rotatable wheel, one or more cables secured to the rotatable wheel, and one or more lift effectors coupled to the first and second chin side supports for lifting the chin side supports in response to rotation of the rotatable wheel in a first rotation direction. A chin piece is provided for supporting a wearer's chin and in turn is supported by the chin side supports. Preferably, the one or more cables are guided for lifting the chin side supports with the use of a capstan and cable guide tubes.

Optionally, the capstans can be in the form of rotating pulleys. Alternatively, the capstans can be fixed pivot pins, if desired. For Also preferably, the one or more cables comprise two cables, one for each chin side support. Alternatively, a single continuous cable can be employed to operate both chin side supports.

Optionally, the cervical collar brace also includes a biasing member for biasing the first and second chin side supports toward a lowered position and wherein the cable adjuster is operable for raising the chin side supports against the biasing of the biasing member. Preferably, the biasing member comprises one or more resilient rubber bands.

In one form the cable adjuster does not restrict the position of the chin side supports to discrete positions relative to the main body collar, but instead is infinitely variable within a range of motion. In another form the cable adjuster restricts the position of the chin side supports to discrete positions relative to the main body collar. In this regard, the rotatable wheel can be secured in discrete positions by hard stops.

Preferably, the one or more cables is/are guided within guide elements formed in or secured to the main body collar. In one preferred form, the guide elements guide one end of the one or more cables through an upper opening through which the cable can be partially drawn to raise the chin side supports relative to the main body collar.

These and other features and advantages of the present invention will become more apparent upon reading the following specification in conjunction with the accompanying drawing figures.

BRIEF DESCRIPTION OF THE DRAWING FIGURES

DETAILED DESCRIPTION OF THE PREFERRED EMBODIMENTS

Figure 1:
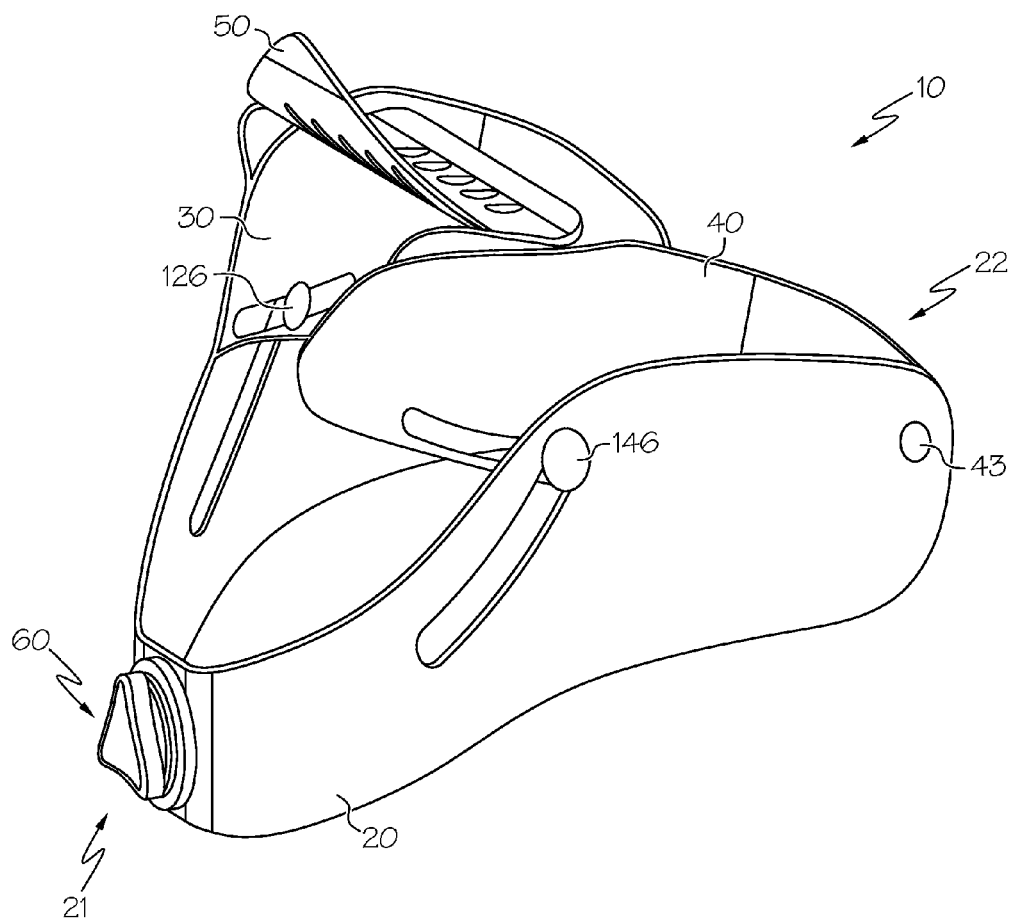
FIG. 1 is a perspective view of a cervical collar brace according to a first example embodiment of the invention.

Referring now to the drawing figures, in which like reference numbers refer to like parts throughout the several views, preferred forms of the present invention will now be described by way of example embodiments. It is to be understood that the embodiments described and depicted herein are only selected examples of the many and various forms that the present invention may take, and that these examples are not intended to be exhaustive or limiting of the claimed invention. Also, as used in the specification including the appended claims, the singular forms "a," "an," and "the" include the plural unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 2:
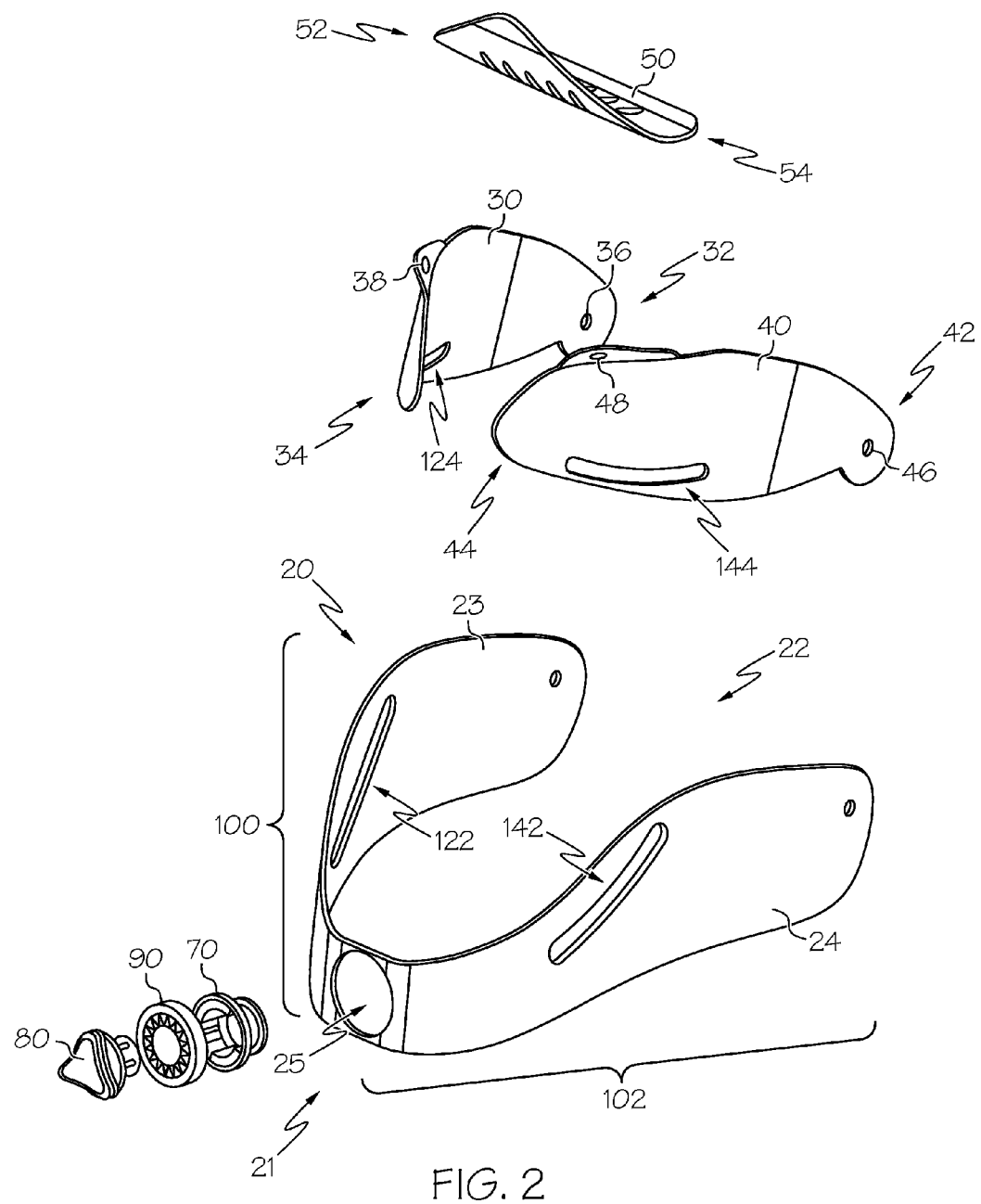
FIG. 2 is a partially exploded perspective view of the orthopedic brace of FIG. 1.
Figure 3:
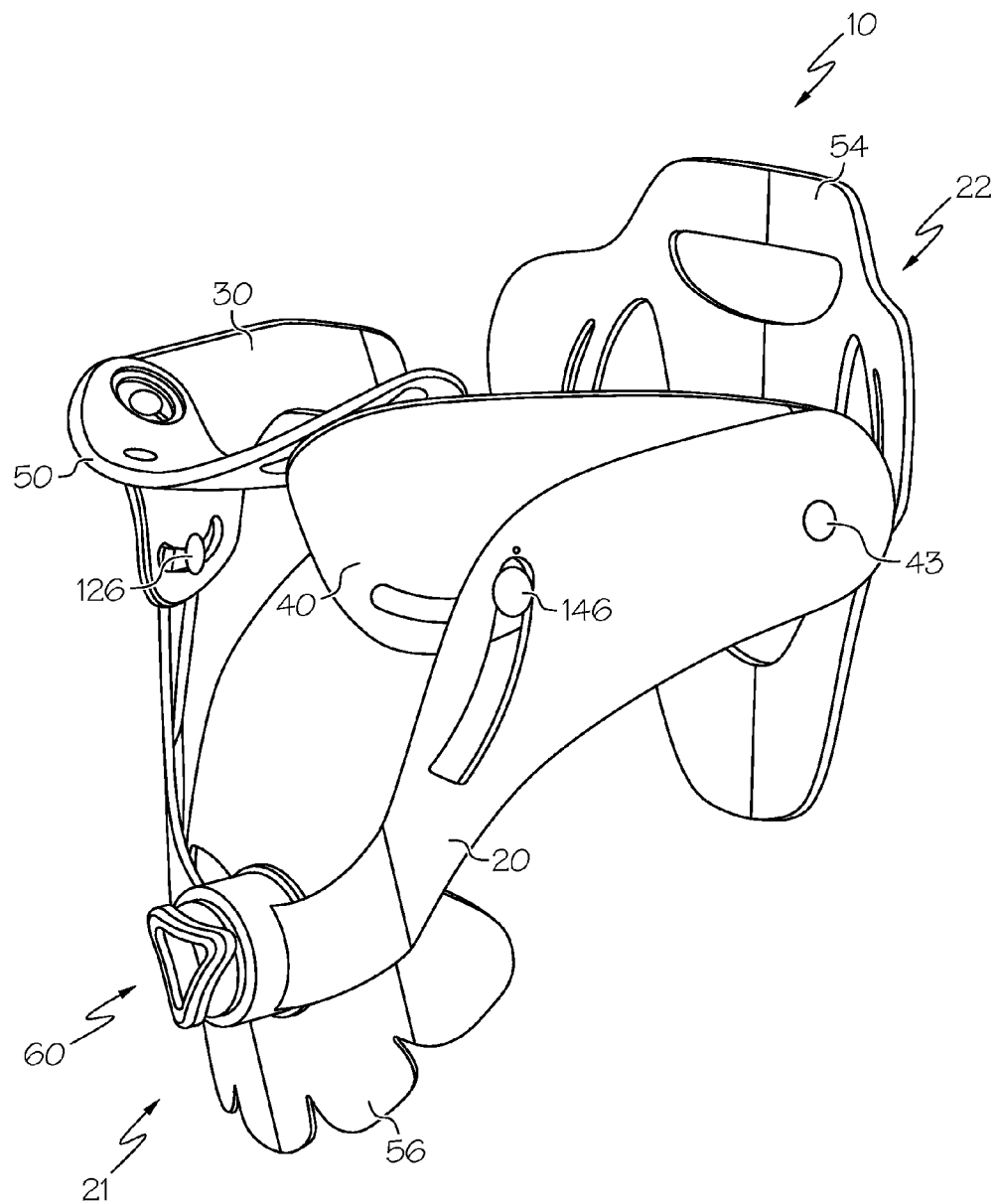
FIG. 3 is a perspective view of another cervical collar brace according to a second example embodiment of the present invention.

With reference now to the drawing figures, wherein like reference numbers represent like parts throughout the several views, FIGS. 1-3 show a cervical collar brace 10 according to a first example embodiment of the present invention. In example embodiments, the cervical collar 10 includes a main collar body 20, a first chin support member 30, a second chin support member 40, a chin piece 50, and a cable adjuster 60.

Typically, the first and second chin supports 30 and 40 pivotally mount to the main collar body 20, and the chin piece 50 pivotally mounts to the first and second chin supports 30, 40. Thus, the chin supports 30 and 40 can pivot relative to the main collar body 20 and the chin piece 50 can pivot relative to the chin supports 30 and 40. The cable adjuster 60 is partially housed within the main collar body 20 and adjustably secures the chin supports 30 and 40 to the main collar body 20. With a single motion of the cable adjuster 60, the chin supports 30 and 40 pivot relative to the main collar body 20, thereby lifting or lowering the pivotally-mounted chin piece 50 to support a wearer's chin. Those skilled in the art will understand that the cervical collar 10 can be made in a variety of sizes and shapes so as to accommodate users of various body sizes.

The main collar body 20 generally comprises a "U-shaped" member having a first (closed) end 21 for placement against a wearer's neck or chest region and a second (open) end 22 for wrapping around the sides of a wearer's neck or head. In typical embodiments, the main collar body 20 has one or more holes, pins, slots or other mounting elements to accommodate mounting or cooperating elements of the collar brace 10. In example embodiments, the first end 21 includes an orifice or aperture 25 formed therein to receive a portion of the cable adjuster 60. The second end 22 includes a first arm 23 and a second arm 24 generally shaped for placement against a wearer's shoulders. Each arm 23, 24 is pivotally mounted to the chin side supports 30, 40. In one form, the pivotal connection is formed by a pivot hole formed in the chin supports 30, 40 and in the arms 23, 24, with pivot pins 33, 43 received in the pivot holes. Also, first slots 122, 142 are formed in the main collar body 20 for accompanying the cable adjuster 60. Optionally, one or more channels, pathways, and/or conduits can be mounted to, within, or partially within the main collar body 20 for guiding a portion of the cable adjuster 60.

The chin supports 30, 40 are generally elongate members having a first end 32, 42 and a second end 34, 44 generally opposite thereto. In example embodiments, the chin supports 30, 40 are mirror images of one another. The first ends 32, 42 of the chin supports 30, 40 have pivot holes 36, 46 to assist in pivotally mounting the same to the pivot holes of the first and second arms 23, 24. The second ends 34, 44 of the chin supports 30, 40 have mounting holes 38, 48 to assist in pivotally mounting the chin piece 50 thereto. Further, the chin supports 30, 40 include second slots 124, 144 formed therein between the first and second ends for accompanying the cable adjuster 60. Preferably, the first end 32 of the first chin support 30 pivotally mounts to the first arm 23 and the first end 42 of the second chin support 40 pivotally mounts to the second arm 24. Various types of pins, screws, clips or other fasteners can be used to pivotally secure the members together. In preferred embodiments, the second ends 34, 44 of the pivotally mounted chin supports 30, 40 generally extend towards the first end 21 of the main collar body 20. In additional example embodiments, one or more channels and/or pathways can be mounted to, within, or partially within the chin supports 30, 40 for guiding a portion of the cable adjuster 60.

The chin piece 50 is a delta-shaped member having a first end 52 and second end 54 generally opposite thereto. The first and second ends 52, 54 have mounting holes to assist in pivotally mounting the same to the second end mounting holes 38, 48 of the chin supports 30, 40. Preferably, one or more pins, screws, clips, or other fasteners pivotally mount the first end 52 mounting hole of the chin piece 50 to the second end mounting hole 38 of the first chin support 30 and the second end 54 mounting hole of the chin piece 50 to the second end mounting hole 48 of the second chin support 40.

The cable adjuster 60 generally includes a rotatable wheel 70, a knob 80, a plurality of mating or catching surfaces 90, cables 100 and 102, and first and second lift effectors 120, 140. In typical embodiments, the rotatable wheel 70 has two cables 100, 102 mounted thereto and pivotally mounts within the aperture 25. In one example, one cable having a sufficient length to reach both lift effectors 120, 140 is mounted to the rotatable wheel 70 at its midpoint. Alternatively, two cables 100, 102 can each be attached to the rotatable wheel 70 and respective lift effectors 120, 140. Free ends of the cables extend to each arm 23, 24 or each chin support 30, 40 where they are mounted to pins 126, 146 for slidably coupling the first slots 122, 142 to the second slots 124, 144. Preferably, the pins 126, 146 are permitted to travel within the slots wherein rotation of the rotatable wheel 70 causes the pins 126, 146 to lift the second ends of the pivotally-mounted chin supports 30, 40 relative to the main collar body 20.

Optionally, the cervical collar 10 can include a posterior member or rear head support 54 for placing against a wearer's rear neck or head (see FIG. 3). Preferably one or more apertures are formed therein to receive a hook or loop material to be removably mounted or secured to a hook or loop material on the collar 10. Further, the first end of the main body collar 20 can include an integral or removably mounted skirt-like flange 56 for additional cushioning support to a wearer's neck or chest region.

Figure 4:
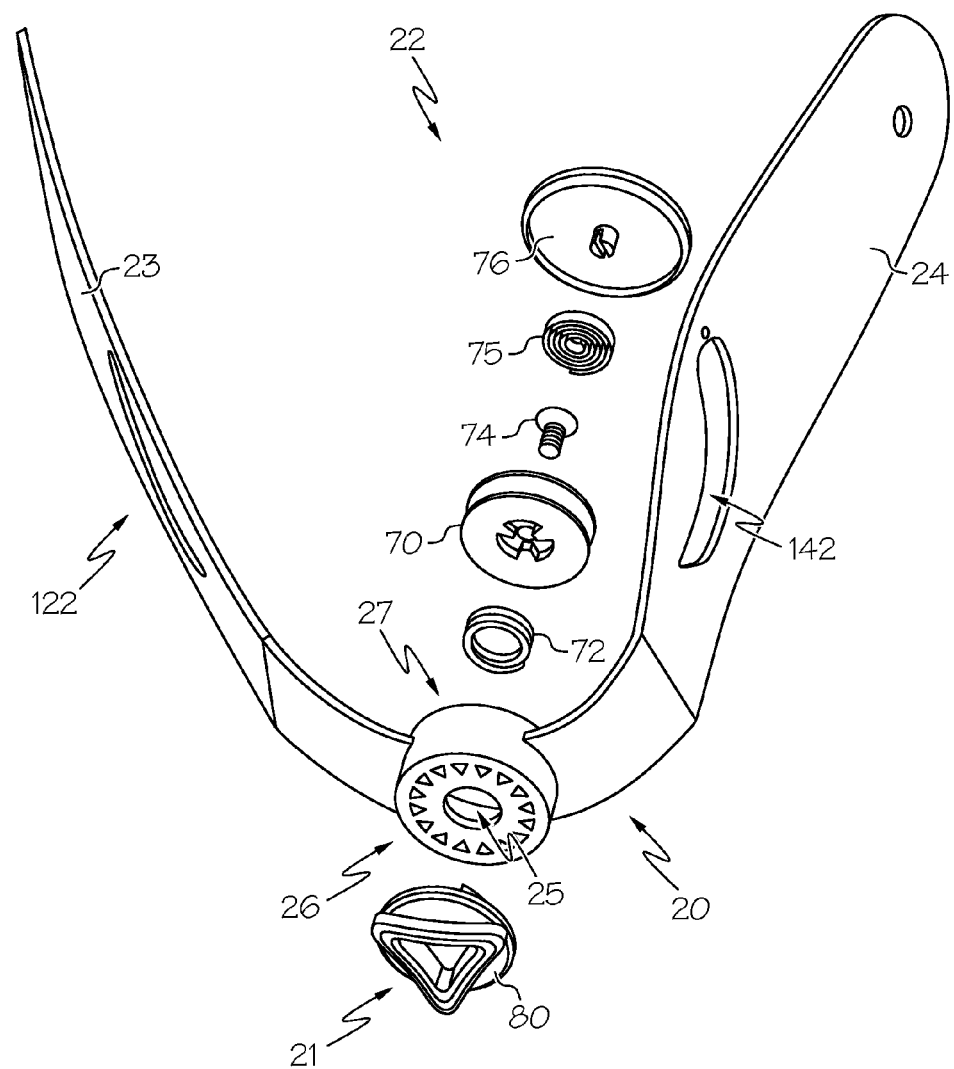
FIG. 4 is a partially exploded perspective view of a portion of the orthopedic brace of FIG. 3.

FIG. 4 shows a portion of the cable adjuster 60 according to a second example embodiment. In general, one or more biasing springs can be mounted within the orifice 25 of the main body collar 20 to control the behavior of the rotatable wheel 70 and one or more elements of the cable adjuster 60 can include mating or catching surfaces to secure the rotatable wheel 70 to particular discrete positions. In typical embodiments, the orifice 25 includes a first end 26 and a second end 27. Optionally, instead of using hand catches to provide discrete stops, one can use smooth friction surfaces to provide infinitely variable positioning. The first end 26 includes one or more catching surfaces or detents 90 surrounding a central opening and the second end 27 includes an opening sized to receive the rotatable wheel 70. Preferably, the opening of the second end 27 is larger than the opening of the first end 26. In additional example embodiments, the orifice 25 can have a substantially similar first and second side and a separate fitting can be used to form one or more catching surfaces or detents 90 (see FIG. 2).

In example embodiments, the rotatable wheel 70 is housed within the second end of the orifice 25 and mounts to a knob 80 positioned close to the first end 26. The knob 80 includes a grasping area to permit a wearer or user to rotate the rotatable wheel 70, indents or catching surfaces to mate with the detents 90 of the first end 26, a central shaft to couple to the rotatable wheel 70, and a bore within the knob to receive a screw or fastener. Preferably, the central shaft of the knob 80 extends through the central opening of the first end 26 of the orifice 25 and mounts within a recessed portion of the rotatable wheel 70. Generally, the central shaft of the knob 80 and the recessed portion of the rotatable wheel 70 have a substantially similar contour to engage and couple to one another. Preferably, the rotatable wheel is secured in discrete positions by the catching surfaces or hard stops. This can be selected by pulling the knob 80 away from the orifice 25, thereby removing the indents from the detents 90, turning the knob to the desired position while remaining disengaged from the detents, and then returning the knob 80 to its unpulled state. Those skilled in the art will further understand that a mechanism permitting the rotatable wheel 70 to be secured in infinitely variable positions (for example a rotatable disc and a selective brake to lock at a desired position) can be used and still be within the scope of the invention.

Additionally, a coil spring 72 can be positioned between the pivotally mounted rotatable wheel 70 and knob 80. Preferably, the coil spring 72 is housed within the second end 27 of the orifice 25 and biases the knob 80 towards the second end 27, thereby preventing the rotatable wheel 70 from rotating by forcing the catching surfaces of the knob 80 and first end 26 of the orifice 25 to engage each other. When it is desired to reposition the rotatable wheel 70, the knob 80 can be pulled away from the orifice and rotated. Optionally, a screw or fastener 74 can be used to further secure the rotatable wheel 70 to the knob 80 and prevent the bias of the coil spring 72 from decoupling the two.

Figure 5:
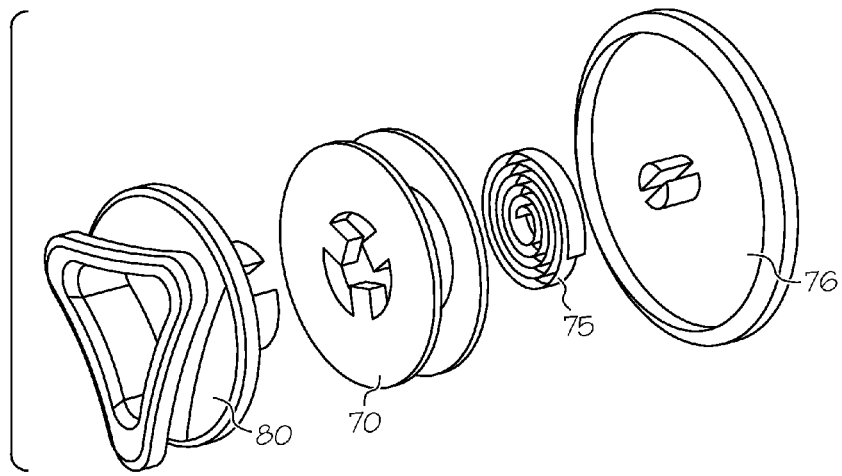
FIG. 5 is a partially exploded perspective view of a portion of the orthopedic brace of FIG. 3.
Figure 6:
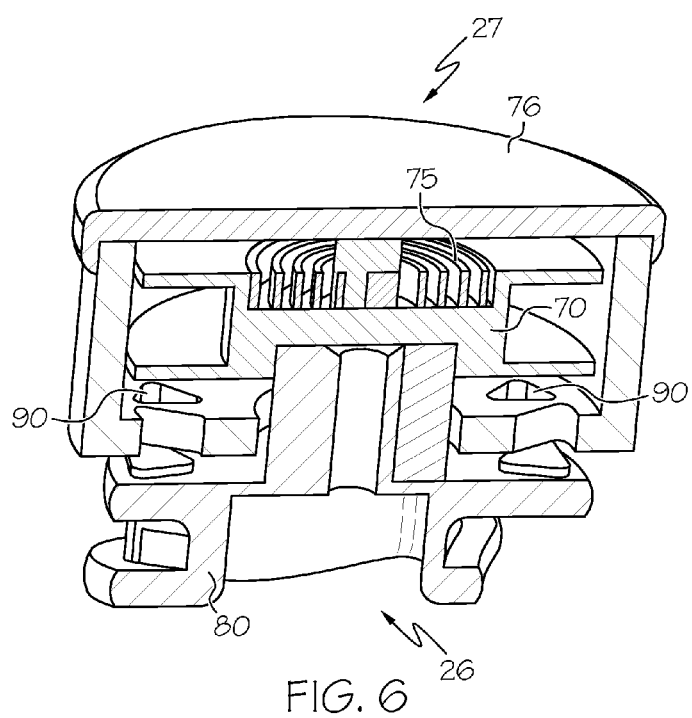
FIG. 6 is a partially cut-away, perspective view of a portion of the orthopedic brace of FIG. 3 according to a third example embodiment of the present invention.

Moreover, a spiral-like torsion spring 75 can couple to the rotatable wheel 70 to bias the wheel towards an unwound position. As depicted in FIGS. 4-6, the torsion spring 75 is housed within a portion of the rotatable wheel 70 and secured by a cap 76. The cap 76 generally includes a central shaft to couple to a central portion of the torsion spring 75 and a perimeter flange to mount to the second end 27 of the orifice 25. For example, as the rotatable wheel 70 is rotated in a first direction, the central shaft of the cap 76 remains stationary, preventing the central portion of the torsion spring from rotating with the rotatable wheel 70, and the outer perimeter of the torsion spring is forced to rotate with the rotatable wheel 70. When the unwound position is desired, the mating surfaces of the orifice first end 26 and the knob 80 are disengaged from one another, and while the mating surfaces remain disengaged by continuously overcoming the bias of the coil spring 72, the knob 80 and coupled rotatable wheel 70 can be easily turned to an unwound position by the bias of the torsion spring 75.

FIG. 6 shows a partial cut-away view of a portion of the cable adjuster 60 according to a third example embodiment. In general, the portion of the cable adjuster 60 includes the orifice 25 comprising one or more detents 90. The rotatable wheel 70 is housed within the second end 27 and coupled to the central shaft of the knob 80. The torsion spring 75 is housed within a portion of the rotatable wheel 70, and the cap 76 encloses the second end 27 and couples to the central portion of the torsion spring 75. In this configuration, the coil spring 72 is removed between the rotatable wheel 70 and the knob 80 wherein the rotatable wheel 70 can be unwound by removing the indents of the knob 80 from the detents 90 a first time. When the original unwound position is desired, the indents of the knob 80 are disengaged from the detents 90 and the knob 80 and the coupled rotatable wheel 70 is freely biased to an unwound position.

Figure 7A:
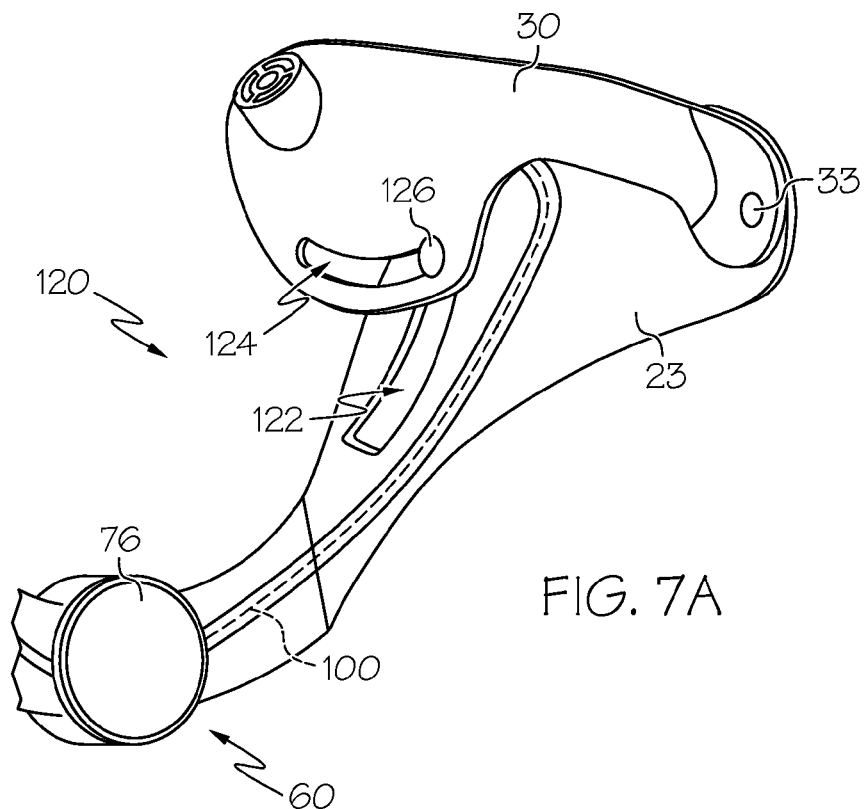
FIG. 7A is a perspective view of a portion of the orthopedic brace of FIG. 3, wherein the support arm is fully lifted.
Figure 7B:
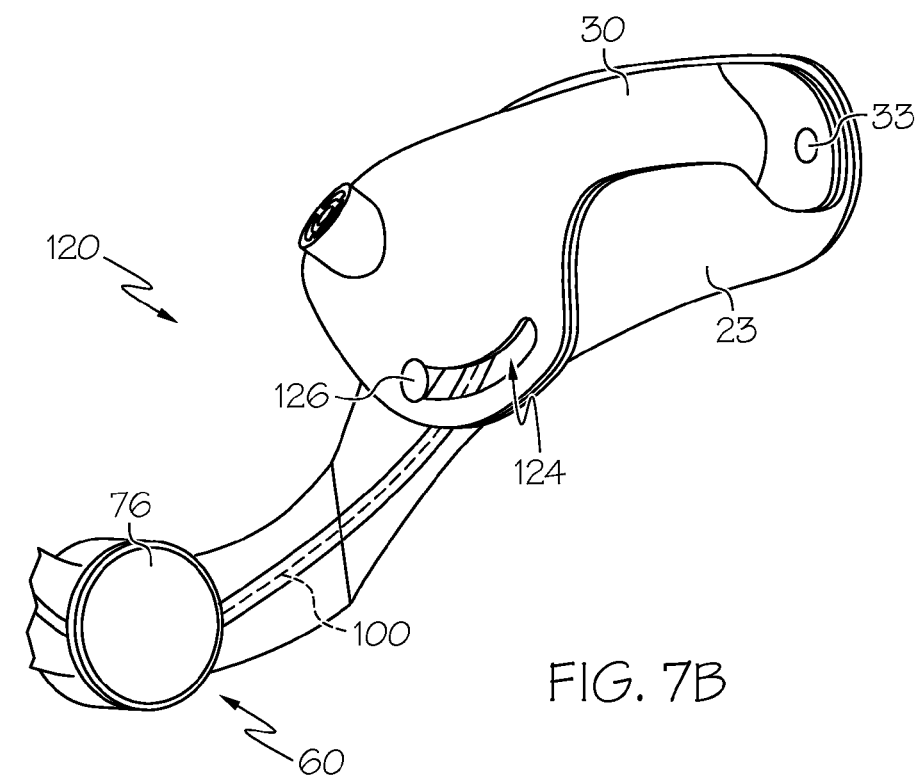
FIG. 7B is a perspective view of a portion of the orthopedic brace of FIG. 3, wherein the support arm is fully lowered.

FIGS. 7A-B show perspective views of the first lift effector 120 including a portion of the main body collar 20 and the pivotally mounted first chin side support 30. As described herein, the first and second lift effectors 120, 140 are mirror images of one another and thus only lift effector 120 will be discussed. Since the cable winding or unwinding around the rotatable wheel 70 actuates both the first and second lift effectors 120, 140, the first and second chin supports 30, 40 move up or down at the same time, at the same rate, and for the same distance. The lift effector 120 includes the first slot 122 formed within the first arm 23 of the main body collar 20, the second slot 124 formed within the first chin side support 30, the pin 126 coupling the slots 122, 124 together, and a cable 100 having a first end mounted to the rotatable wheel 70 and a second end mounted to the pin 126. From a lowered position (rotatable wheel unwound), the pin 126 is driven within the first slot 122 by turning the rotatable wheel 70 (see FIG. 7B). Subsequently, as the pin 126 is forced to travel within the first slot 122, the second slot 124 is forced to adjust accordingly, thereby lifting the pivotally mounted chin support 30 (see FIG. 7A). Those skilled in the art will further understand that slots of a variety of shapes, sizes or configurations can be used and still be within the scope of the invention. Those skilled in the art will further understand that pins of many shapes, sizes, forms, configurations or frictional-fits can be used and still be within the scope of the invention.

Optionally, the slots can include one or more catching surfaces or indents to interact with a portion of the cable adjuster 60, for example to maintain a particular position of the chin supports 30, 40 if the catching surfaces or indents 90 of the cable adjuster 60 were released unintentionally, permitting the rotatable wheel 70 to unwind.

Figure 8:
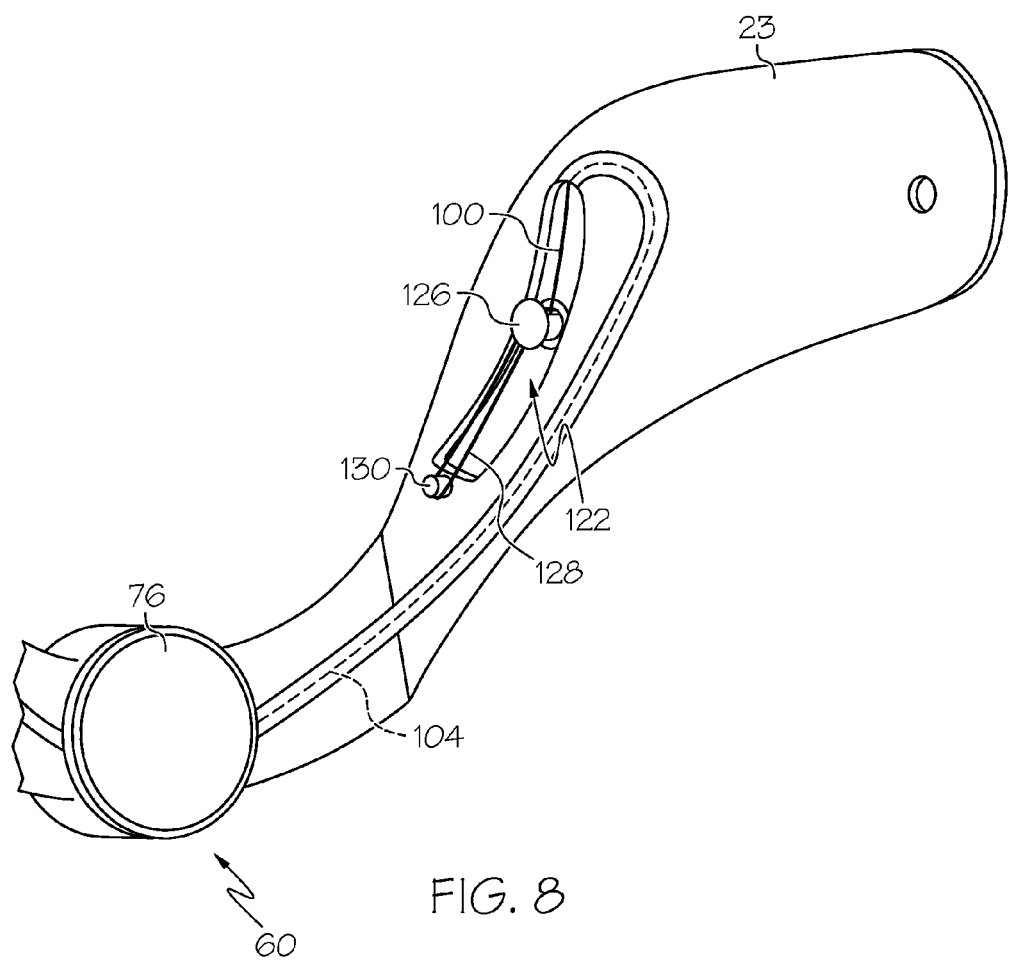
FIG. 8 is a perspective view of a portion of the cable adjuster of the orthopedic brace of FIG. 3 according to a fourth example embodiment of the present invention.

FIG. 8 shows a perspective view of a portion of the first lift effector 120 according to a fourth example embodiment. As described herein, the first and second lift effectors 120, 140 are mirror images of one another and thus only lift effector 120 will be discussed. In example embodiments, the cord 100 is guided from the rotatable wheel 70 to a top portion of the first slot 122 through a conduit or tube 104, for example like a Bowden cable used to operate a bicycle braking system. The tube 104 can be mounted to, within, or partially within the main collar body 20. Further, the cord extends within or near the slot 122 and mounts to the pin 126. The cord 100 can be mounted to the pin by tying a knot, a loop, a looped or notched member within or extending from the pin 126, or by any other connector. As the rotatable wheel 70 is turned, the cable 100 is drawn and raises the pin 126, further raising the chin support 30 (see FIG. 7A).

In additional example embodiments, the lift effectors 120, 140 can include one or more biasing members for biasing the first and second chin supports 30, 40 towards a lowered position. As depicted in FIG. 8, a biasing member or resilient rubber band 128 is mounted to the pin 126 at a first end and to a post 130 at a second end. The biasing member 128 biases the pin 126 towards a bottom portion of the slot 122, thereby biasing the pivotally mounted first chin support 30 toward a lowered position. Preferably, the bias of the biasing member 128 is adjusted to permit the cable adjuster 60 to operate. Those skilled in the art will understand that one or more gears could be used to reduce the rotational force required to overcome the bias of the biasing member 128.

Figure 9:
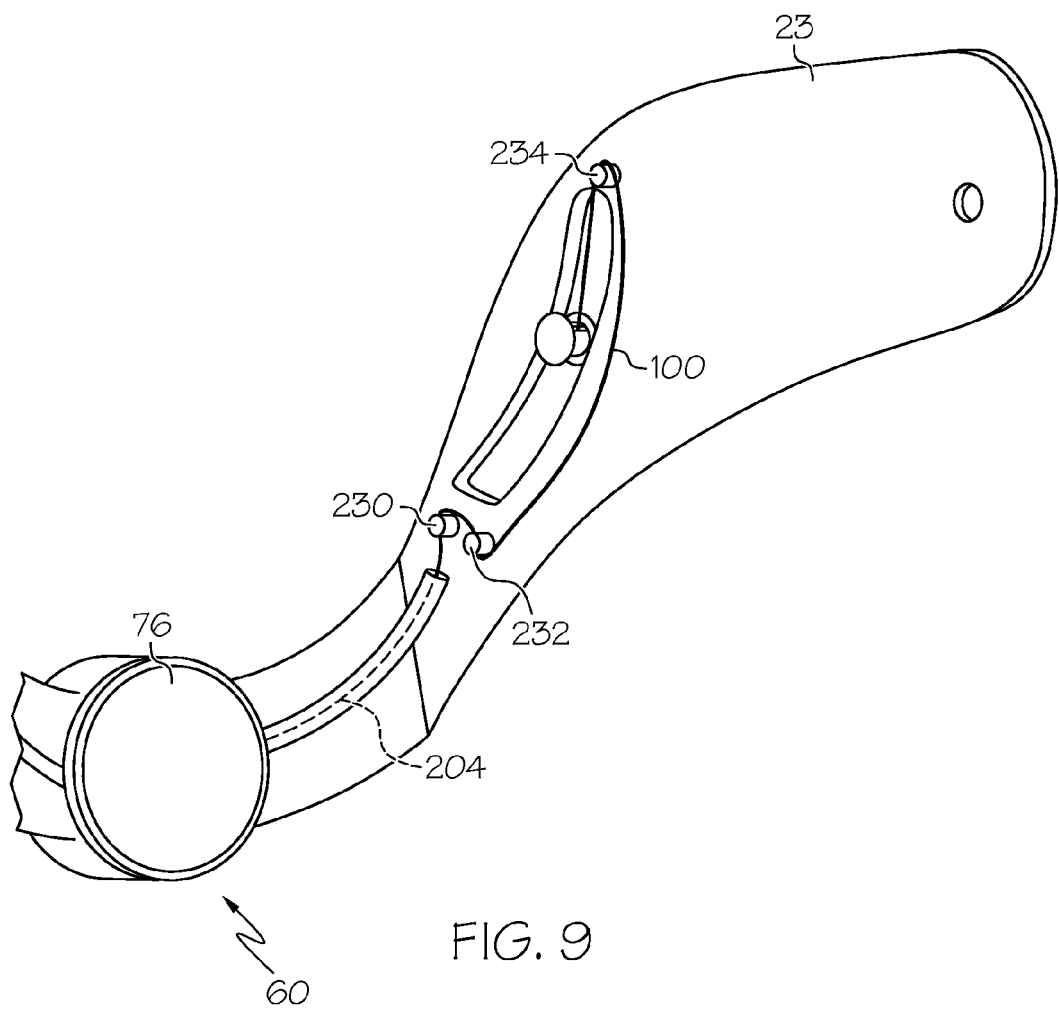
FIG. 9 is a perspective view of a portion of the cable adjuster of the orthopedic brace of FIG. 3 according to a fifth example embodiment of the present invention.

FIG. 9 shows a perspective view of a portion of the first lift effector 120 according to a fifth example embodiment. In example embodiments, the cord 100 is guided from the rotatable wheel 70 to a generally central portion of the first arm 23 through a conduit or tube 204, for example a Bowden cable. Further, the cord extends from the end of the generally centrally-positioned tube 204 and passes around one or more structures or connectors before mounting to the pin 126. For example, the cord 100 passes around a first post 230 and under a second post 232 (generally forming a backwards "S" shape), and further passes over a third post 234 close to the top portion of the slot 122 before mounting to the pin 126. Preferably, the posts have one or more apertures to thread and guide the cord 100 therethrough. Additionally, the cord 100 can be mounted to the pin by tying a knot, a loop, a looped or notched member within or extending from the pin 126, or by any other connector. Similarly, as the rotatable wheel 70 is turned, the cable 100 is drawn and raises the pin 126, further raising the chin support 30 (see FIG. 7A). Those skilled in the art will understand that one or more pulleys, guides, or friction-reducing elements can be used and still be within the scope of the invention.

In additional example embodiments, the cable 100 can further extend to the second slots 124, 144 of the first and second lift effectors 120, 140. In example embodiments, the cable 100 can be guided close to the second slots 124, 144 through a tube (e.g., like tube 104 or 204). In this manner, by turning the rotatable wheel 70, the pin (e.g., like pin 126, 146) is forced to travel within the second slots 124, 144, and the first slots 122, 142 are forced to adjust accordingly. Additionally, the cable 100 can be guided through the pivots where the first and second chin supports 30, 40 are mounted to the arms 23, 24 of the main collar body 20.

In commercial embodiments, the elements of the cervical collar 10 are generally made of a plastic (e.g., polyethylene, thermoplastic, etc.) or other materials transparent to X-Ray, computed tomography, and magnetic resonance imaging. The cervical collar 10 can also include one or more removable pads for additional comfort and support to a wearer or user. Preferably, the removable pads are made of a laminated foam material or a material suitable to wick away moisture and to reduce skin irritation. In example embodiments, one side of the removable pads comprises a loop material (or fabric having a weave that cooperates with hook material) and one side comprises a material suitable to be placed against the skin of a user or wearer. Any portion of the main collar body 20, first or second chin support 30, 40, chin piece 50, optional rear head support 54, and/or optional flange 56 can include hook material for cooperating with the loop material of the one or more removable pads.

Figure 10:
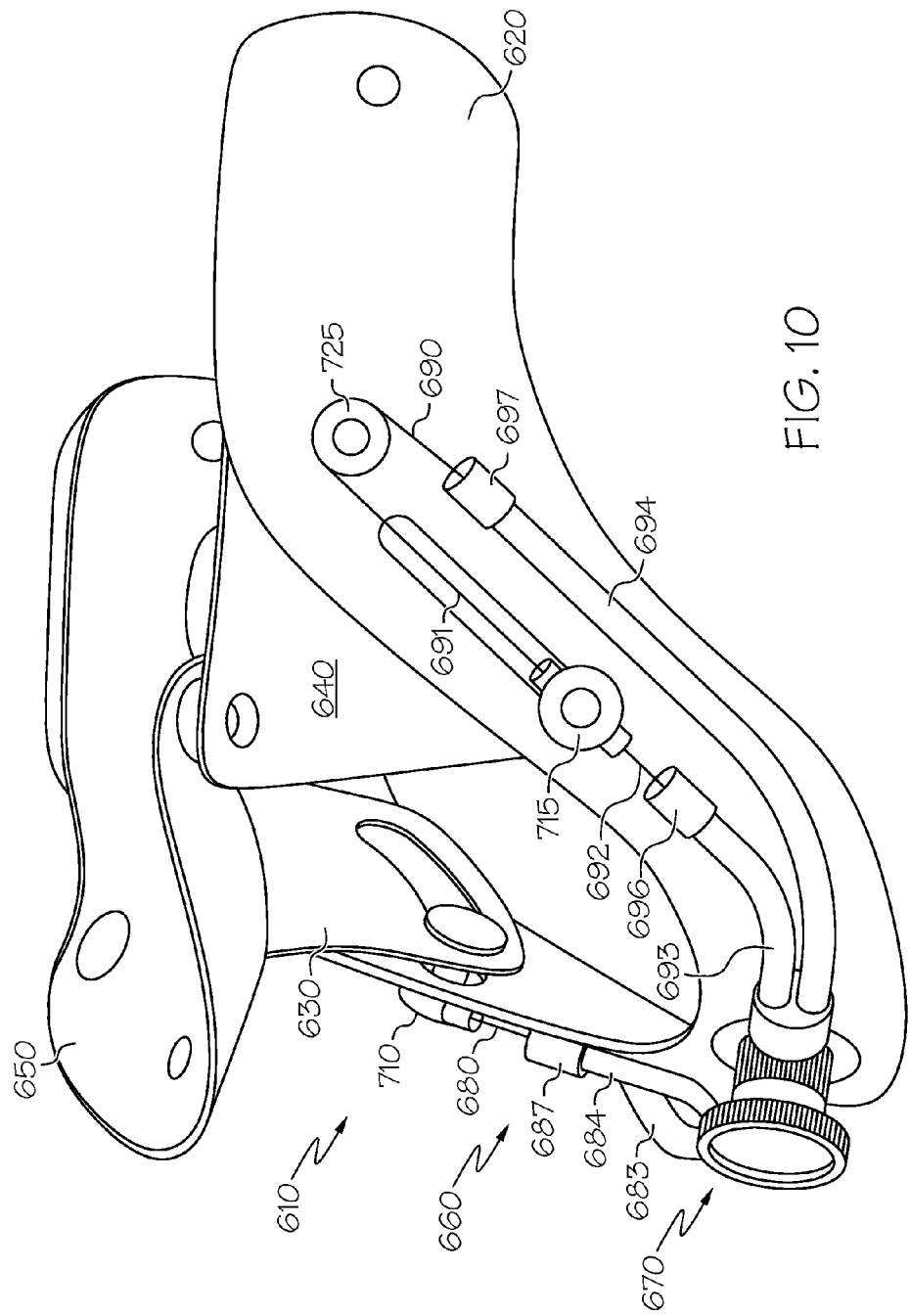
FIG. 10 is a right side perspective view of a cervical collar brace according to a sixth example embodiment of the invention.
Figure 11:
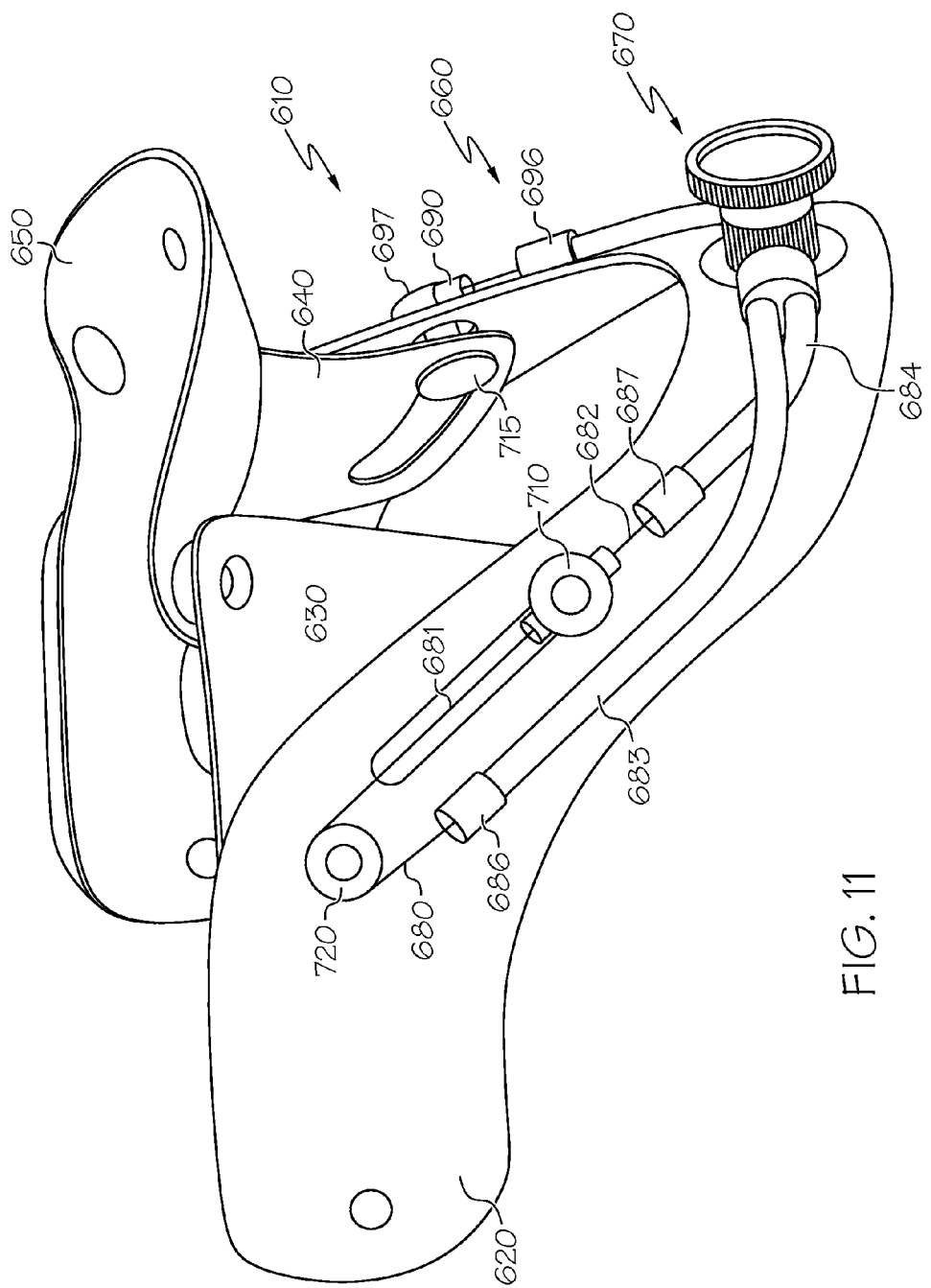
FIG. 11 is a left side perspective view of the orthopedic brace of FIG. 10.
Figure 12:
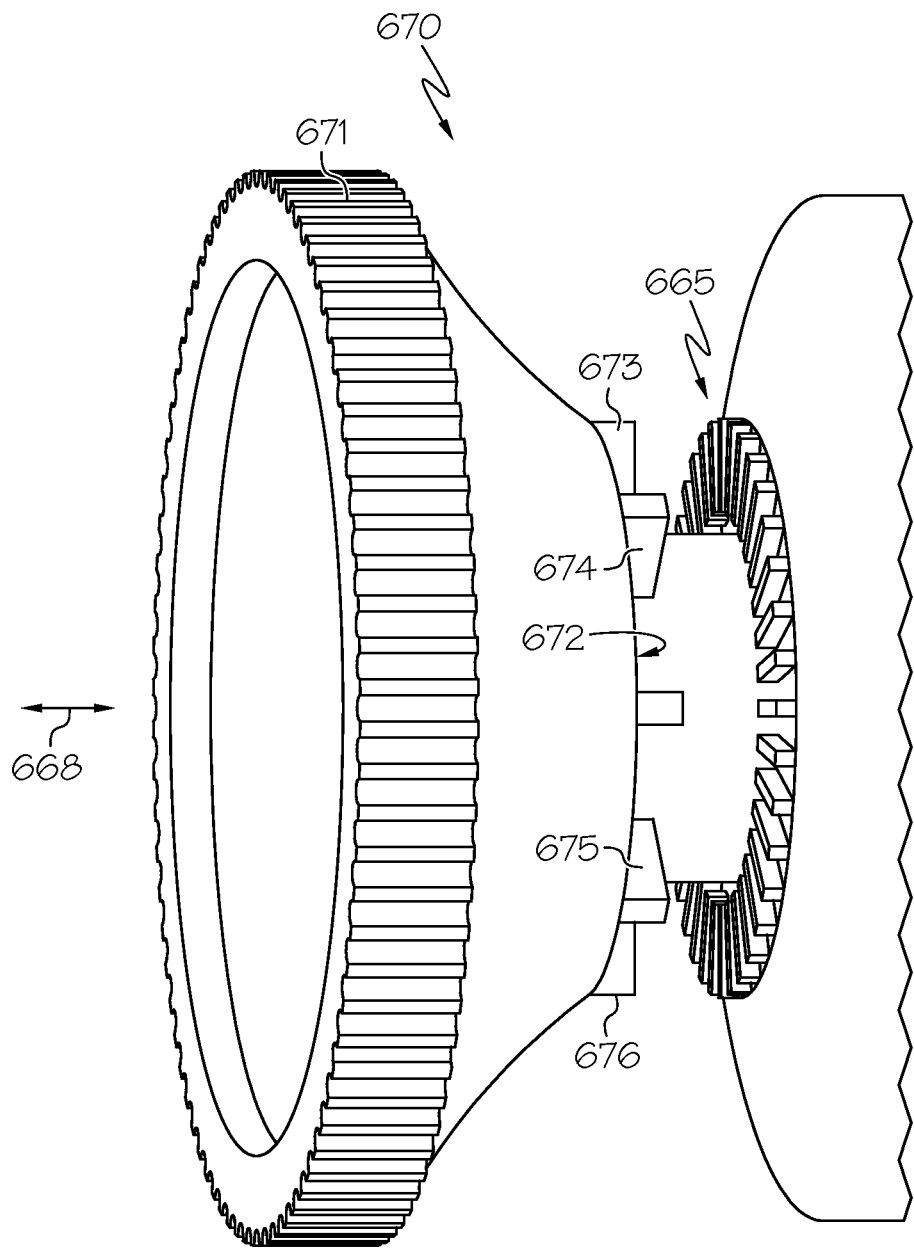
FIG. 12 is a close up perspective view of a portion of the orthopedic brace of FIG. 10.

FIGS. 10-12 show a cervical collar brace 610 according to a sixth example embodiment of the present invention. The cervical collar 610 includes a main collar body 620, a first chin support member 630, a second chin support member 640, a chin piece 650, and a cable adjuster 660. The first and second chin supports 630 and 640 are pivotally mounted relative to the main collar body 620, and the chin piece 650 is pivotally mounted relative to the first and second chin supports 630, 640. Thus, the chin supports 630 and 640 can pivot relative to the main collar body 620 and the chin piece 650 can pivot relative to the chin supports 630 and 640.

The cable adjuster 660 is mounted to the main collar body 620 and adjustably secures the chin supports 630 and 640 to the main collar body 620. With a single motion of the cable adjuster 660, the chin supports 630 and 640 pivot relative to the main collar body 620, thereby lifting or lowering the pivotally-mounted chin piece 650 to support a wearer's chin. The cable adjuster 660 includes a rotatable wheel 670 or knob and a pair of cables 680, 690 secured to the rotatable wheel 670.

A pair of lift effectors 710, 715 are coupled to the first and second chin side supports for lifting or lowering the chin side supports in response to rotation of the rotatable wheel 670. Two capstans 720, 725 are positioned above the lift effectors 710, 715 for reversing a movement of the ends of the cables. In this example embodiment, the capstans comprise rotatable pulleys. Alternatively, the capstans can comprise fixed pins over which the cables are looped for sliding motion.

The two cables 680, 690 each include first and second end portions, with the first end portion secured to a lift effector for pulling the lift effector in one direction and the second portion secured to the lift effector for pulling the lift effector in a second direction, opposite to the first direction. For example, as shown in FIG. 10, the single cable 690 has a first end 691 for lifting the lift effector and a second end 692 for pulling the lift effector downwardly. Optionally, the cables run in fixed tubes (secured to the collar body 620) to keep the cables reasonably taut and allow movement of the cables to be turned into movement of the lift effectors (by preventing the cables from assuming a different overall shape/orientation as they are pulled in one direction or another). See for example the fixed tubes 683, 684, 693, 694. As mentioned above, these can be in the form of Bowden tubes. The tubes are secured at their ends to the main collar body 620, such as by ferrules 686, 687, 696, 697.

Preferably, each cable is arranged in a race-track configuration, and each cable includes first and second end portions, with the first portion secured to a lift effector for pulling the lift effector in one direction and the second portion secured to the lift effector for pulling the lift effector in a second direction, opposite to the first direction. Thus, preferably, each cable is a single cable and its two ends are each attached to the lift effector such that moving the race-track cable in one direction lifts the lift effector and moving the cable in the opposite direction lowers the lift effector (and thus the chin piece). Preferably, the rotatable wheel is connected to an internal axle and the cables are wrapped around the axle such that rotation of the rotatable wheel in one direction causes the cables to pull up on the lift effectors and rotation of the rotatable wheel in an opposite direction causes the cables to pull down on the lift effectors.

FIG. 12 shows the cable adjuster's rotatable wheel 670 in greater detail. As depicted in this figure, the wheel 670 has a knurled or serrated circumferential edge 671 and a toothed rear surface 672. Those skilled in the art will recognize that the rotatable wheel or knob can take various forms/shapes for convenience, aesthetics, or ergonomics. The toothed rear surface carries a small number of radially projecting teeth on the annular rear surface 672, such as teeth 673, 674, 675, 676. These teeth are adapted to engage a circular array of teeth 665. Thus, the cable adjuster is movable between various discrete positions, and thereby restricts the position of the chin side supports to discrete positions relative to the main body collar.

In other words, the rotatable wheel portion of the cable adjuster is secured in discrete positions by hard stops (the teeth). The rotatable wheel is secured in these discrete positions by hard stops which are selected by pulling out on the rotatable wheel and turning the rotatable wheel while it is pulled out and then returning the rotatable wheel to its unpulled state. Thus, the wheel can be pulled out along axis 668, rotated about the axis 668 to achieve the desired adjustment in the height of the chin piece, and the wheel can be moved back into a locked position (with the teeth engaged with one another) by returning the wheel along axis 668. Preferably, a spring is provided for biasing the wheel toward its retracted position in which the teeth 673-676 are engaged with the circular array of teeth 665.

Figure 13:
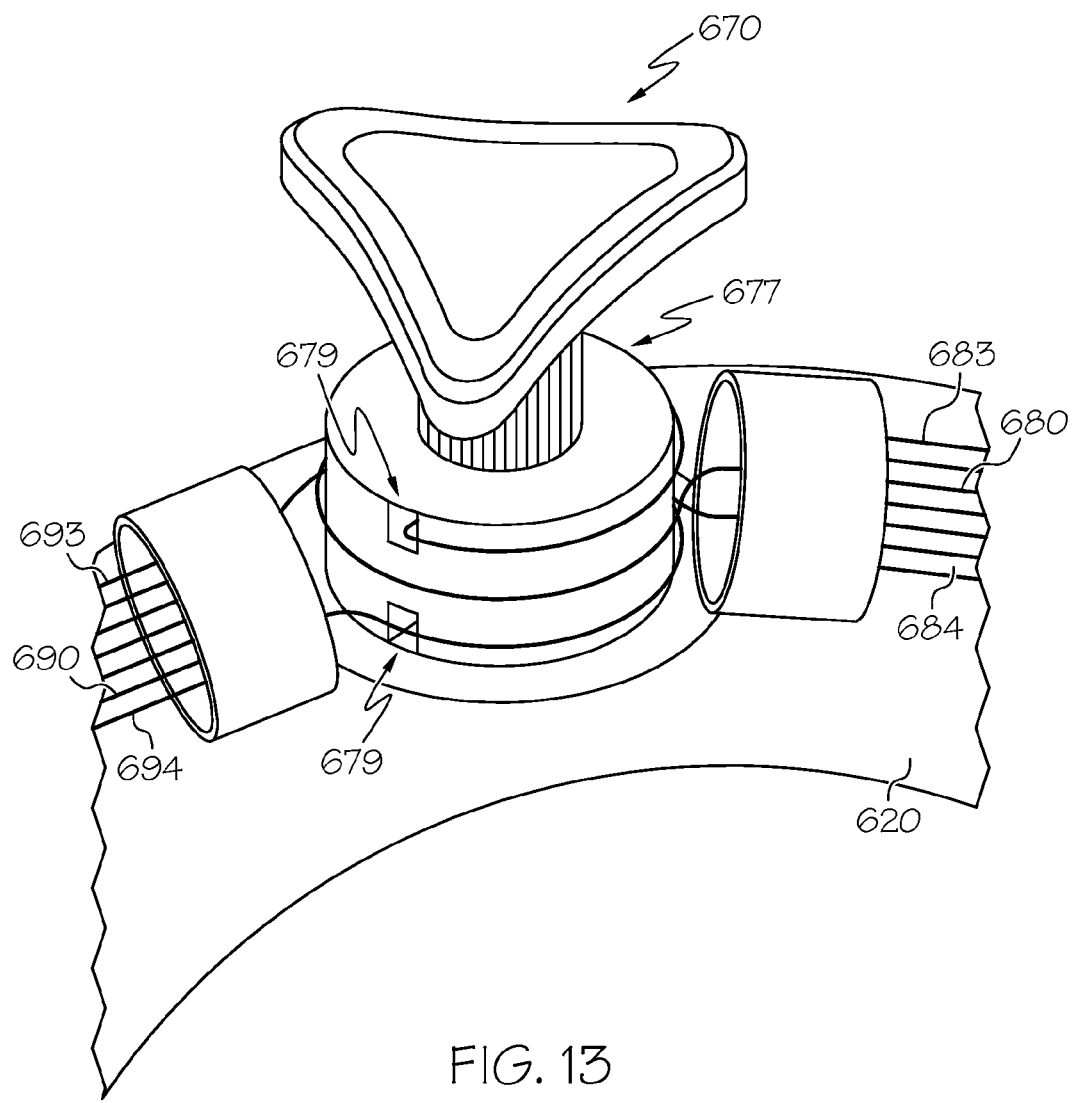
FIG. 13 is a close up perspective view of a portion of the orthopedic brace of FIG. 10, showing the connection of cables with the rotatable wheel.

FIG. 13 shows the connection of the cables 680, 690 with the rotatable wheel 670 in greater detail. As depicted in this figure, an internal axle or drum 677 of the rotatable wheel 670 provides for the connection of the single cables 680, 690. In one form, the single cables 680, 690 engage slots 679 formed along the periphery of the axle 677. As such, the slots 679 ensure the cables 680, 690 remain engaged therewith such that motion of the rotatable wheel 670 causes movement of the ends 681, 682, 691, 692 of the cables 680, 690. In other forms, the single cables 680, 690 may be cut or separated as desired, for example, wherein an end opposite of the end 691 is connected to one slot and wherein an end opposite the end 692 is connected to another slot of the axle 677. In example forms, a knot or cord protrusion can be provided to ensure that the cords remain engaged with the slots 679. Optionally, glues, adhesives or other forms of connecting or coupling additives can be used with the cables 680, 690 and slots 679 as desired.

In FIGS. 10-13, the collar is shown with an outer covering thereof removed, for clarity of illustration such that the cables and the tubes are depicted as mounted on an inside portion of the collar. In a commercial embodiment of this invention, it is expected that the tubes and cables will be covered with an outer covering.

Applicants have found that this embodiment of FIGS. 10-13 provides an exceptionally smooth adjustment of the chin piece, while also providing secure positioning thereof.

While the invention has been described with reference to preferred and example embodiments, it will be understood by those skilled in the art that a variety of modifications, additions and deletions are within the scope of the invention, as defined by the following claims.

What is claimed is:

1. A cervical collar brace comprising:
    a one-piece main body collar;
    a first chin side support pivotally mounted relative to the main body collar;
    a second chin side support pivotally mounted relative to the main body collar;
    a chin piece for supporting a wearer's chin and supported by the chin supports; and
    a cable adjuster for adjustably securing the first and second chin side supports relative to the main body collar, the cable adjuster comprising a rotatable wheel, one or more cables operated by the rotatable wheel, one or more lift effectors coupled to the first and second chin side supports for lifting the chin side supports in response to rotation of the rotatable wheel in a first rotation direction,
    wherein rotation of the rotatable wheel in the first rotational direction causes the cables to provide movement to the first chin side support in a first pivotal direction and provide movement to the second chin side support in a second pivotal direction generally opposite the first pivotal direction, and wherein pivotal movement of the first and second chin side supports in the first and second pivotal directions when viewing front sides thereof, respectively, is generally equal and opposite relative thereto in an upward and lifting direction.

2. The cervical collar brace as claimed in claim 1 wherein the cable adjuster is movable between various discrete positions, and thereby restricts the chin side supports to discrete positions relative to the main body collar.

3. The cervical collar brace as claimed in claim 2 wherein the rotatable wheel of the cable adjuster is secured in discrete positions by hard stops.

4. The cervical collar brace as claimed in claim 3 wherein the rotatable wheel is secured in discrete positions by hard stops which are selected by pulling out on the rotatable wheel and turning the rotatable wheel while it is pulled out and then returning the rotatable wheel to its unpulled state.

5. The cervical collar brace as claimed in claim 1 further comprising guide elements formed in or secured to the main body collar and wherein the one or more cables is/are guided within guide elements.

6. The cervical collar brace as claimed in claim 5 wherein the guide elements comprise fixed guide tubes.

7. The cervical collar brace as claimed in claim 5 wherein the guide elements guide one end of the one or more cables through an upper opening through which the cable can be partially drawn to raise the chin side supports relative to the main body collar.

8. The cervical collar as claimed in claim 1 further comprising one or more capstans positioned above the lift effectors for reversing a movement of at least one end of one or more cables.

9. The cervical collar brace as claimed in claim 8 wherein the one or more capstans comprise one or more rotatable pulleys.

10. The cervical collar brace as claimed in claim 8 wherein the one or more capstans comprise one or more fixed pins over which the one or more cables are looped.

11. The cervical collar brace as claimed in claim 1 wherein the one or more cables comprise two cables, one for each chin side support.

12. The cervical collar brace as claimed in claim 11 wherein the two cables each include first and second portions, with the first portion secured to a lift effector for pulling the lift effector in one direction and the second portion secured to the lift effector for pulling the lift effector in a second direction, opposite to the first direction.

13. The cervical collar brace as claimed in claim 1 wherein the one or more cables comprise two cables, one for each chin side support, with each cable being arranged in a race-track configuration, and wherein each cable includes first and second portions, with the first portion secured to a lift effector for pulling the lift effector in one direction and the second portion secured to the lift effector for pulling the lift effector in a second direction, opposite to the first direction.

14. The cervical collar brace as claimed in claim 13 wherein the rotatable wheel is connected to an internal axle and the cables are wrapped around the axle such that rotation of the rotatable wheel in one direction causes the cables to pull up on the lift effectors and rotation of the rotatable wheel in an opposite direction causes the cables to pull down on the lift effectors.

15. The cervical collar brace as claimed in claim 1 further comprising biasing members for biasing the lift effectors, and wherein rotation of the rotatable wheel in the first rotational direction causes the cables to pull the lift effectors in a direction that is generally against a bias of the biasing members.

16. The cervical collar brace as claimed in claim 1 wherein a force being applied to the chin piece causes movement to the lift effectors in a first direction, and wherein rotation of the rotatable wheel in the first rotational direction causes the cables to be forced against the first direction in a second direction.

* * * * *